United States Patent [19]

Ghyczy et al.

[11] Patent Number: 5,129,950

[45] Date of Patent: Jul. 14, 1992

[54] PROCESS OF IMPROVING ACTIVITY OF HERBICIDES AND FERTILIZERS USING N-(2-HYDROXYETHYL)-ACETAMIDE OR -PROPANAMIDE

[75] Inventors: Miklos Ghyczy; Jörg Hager, both of Cologne, Fed. Rep. of Germany

[73] Assignee: A Nattermann & Cie GmbH, Cologne, Fed. Rep. of Germany

[21] Appl. No.: 623,276

[22] Filed: Dec. 6, 1990

Related U.S. Application Data

[63] Continuation of Ser. No. 111,787, filed as PCT/EP87/00010, Jan. 10, 1987, abandoned.

[30] Foreign Application Priority Data

Jan. 13, 1986 [DE] Fed. Rep. of Germany ....... 3600664

[51] Int. Cl.$^5$ ...................... A01N 37/20; A01N 47/30
[52] U.S. Cl. ......................................... 71/118; 71/120; 71/DIG. 1
[58] Field of Search ................... 71/120, 118, DIG. 1

[56] References Cited

U.S. PATENT DOCUMENTS 4,454,073 6/1984 Lewis .............................. 260/501.21
4,681,617 7/1987 Ghyczy et al. ......................... 71/86

OTHER PUBLICATIONS

Brian et al. CAS 55:2991d (1959).
Brian et al. CAS 78:68237y (1972).
McCutcheon's Emulsifiers and Detergents Handbook 1981, pp. 136–139.
CAS Index Guide, 1984, p. 1243 G. col. 1.
*Agrachemicals Handbook*, 1983, "Fonuron".
Attwood et al. 1983 in: Surfactant Systems, Their Chemistry, Pharmacy, and Biology. Chapman and Hall. New York pp. 1—37, 389-463, 678-691.
*Encylopedia of Chemical Technology*, Third Edition, vol. 2, John Wiley & Sons, New York, pp. 252-258.

*Primary Examiner*—Allen J. Robinson
*Assistant Examiner*—S. Mark Clardy
*Attorney, Agent, or Firm*—Pearne, Gordon, McCoy & Granger

[57] ABSTRACT

The invention is related to the use of certain water-soluble compounds known as such and having the Formula $$R^1-CO-NH-R^2$$

for the modulation of membrane dependent metabolism processes within living cells, in particular with relation to transport phenomena and cell procedures which are induced or influenced by active agents supplied from outside the cell, products containing these substances for the above described uses and processes using these products.

2 Claims, No Drawings

PROCESS OF IMPROVING ACTIVITY OF HERBICIDES AND FERTILIZERS USING N-(2-HYDROXYETHYL)-ACETAMIDE OR -PROPANAMIDE

This is a continuation of application Ser. No. 111,787, filed Sept. 9, 1987 now abandoned.

The invention is related to the use of known compounds for the modulation of membrane dependent metabolism processes with living cells. Of particular importance are product transport phenomena as well as certain cell processes induced by active agents supplied from outside of the cell (f.i. growth promoting agents, growth inhibiting agents, herbicides, fungicides, bactercides, fertilizers). By the combination of the membrane modulators according to the invention with such compounds it is possible to influence the activity of these compounds, probably by an influence the activity of these compounds, probably by an influence upon these cell processes in the desired direction, i.e. they enlarge, suppress, accelerate or slow down such cell processes. For instance, the following cell processes may be modulated by the compounds of the invention:

- the transportation of nutriments,
- the transport of hydrogen ions,
- the transportation of water and/or ions,
- the endocytose and exocytose,
- the turn over speed of membrane controlled enzymes
- the transport of active agents (growth agents, growth inhibitors and the like).

Surprisingly, the cell membrane of plant cells or animal cells or fungus cells may be influenced in a desired manner. Thus, plants may be caused to a quicker growth when influencing the growth limiting factors of the uptake of nutriments. On the other hand, cells which have lost the ability of controlled growth such a tumor cells thus could be inhibited in their undesired growth properties.

The uptake of agents influencing the development of cells such as drugs or plant protecting agents could substantially be increased.

Many attempts therefore have been made to find compounds which influence cell membranes in the above mentioned manner. In particular those compounds have to be mentioned which are components of the membrane or present in the membranes such as the phospholipids making up to 70% of the cell membrane. Fractions of phospholipids have also been tried.

European patent application EP 74 251 describes that particular fractions of phospholipids and triglycerides may lower the fludity of cell membranes. The following diseases or changes in the metabolism are described to be possibly influenced: Alcoholism, drug dependency, disturbances in the immune system, disturbances of the nervous system, high blood pressure, atherosclerosis.

In the German published patent application DE-OS 31 50 296 there is described the use of quaternary ammonium salts such as choline chloride to influence the fluidity of membranes in the plant and thus make them more sensitive to cold temperatures.

As described in PROTOPLASMA 50, (1976), pgs. 229 ff., tomato plants by the addition of ethanolamine, a component of the phospholipid cephaline, may be made less sensible to damage caused by low temperatures.

In the DDR patents DD 209340, DD 208038 and DD 209339 it is reported that choline chloride and ethanolamine may be used along or together, possibly in combination with other substances to influence positively the houshold water and the growth of the plants. The disadvantage of these substances is that the desired effect only is obtained when using them at high concentration. Thus, DDR patent DD 209339 describes that choline and ethanolamine are used in amounts of 6 kg/ha. These high amounts are not only uneconomical but also undesirable environmentally.

It is therefore an object of the present invention to find compounds which at dosages as small as possible modulate the cell membranes, in particular modulate cell membrane dependent metabolism processes within living cells, in particular with relation to transport phenomena and cell procedures which are induced or influenced by active agents supplied from outside the cell and processes in the cell membrane which not only unspecifically lower the fluidity of the membrane wall but, dependent upon the applied dosage by way of an increase or lowering of the permeability of cell membranes, influence the processes occuring in the cell in an optimal manner and degree to produce the desired result.

It is most desirable and a prerequisite environmentally of such an influence that such products are non-toxic. They should be easily available or be easily produced and formulated.

According to the invention, there are used to modulate cell membranes as above described, the selected group of simple water-soluble, partially naturally occuring compounds according to the general Formula I

$$R^1-CO-NH-R^2$$

wherein $R^1$ is a straight or branched, saturated or unsaturated alkyl with 1 to 6 carbon atoms or an acyloxyalkyl with 1 to 3 atoms both in the acyl and in the alkyl group. Preferably, $R^1$ is methyl, ethyl or propyl and $R^2$ is methyl, ethyl, 2-hydroxyethyl, 2-acetyloxyethyl, 2-hydroxypropyl or 3-hydroxypropyl.

Particularly preferred are N-acetylethanolamine and N-methylacetamide. They may be used together. If so, this mixture contains the components in a weight proportion of from 1:10 to 10:1.

The cell membrane modulating properties of the compounds used according to the invention are shown by the following tests and test results:

1. In a Petri dish there are mixed a potato dextrose agar substrate with 0.1 ppm of 2,4'-dichloro--(pyrimidin-5-yl)-benzhydryl alcohol (generic name: Fenarimol). This active agent is a known product, against plant pathogenic fungi in particular. A suspension of the fungus *Botrytis cinera* is mixed with an increasing amount of N-acetylethanolamine and two droplets of these mixtures are placed in the middle of the Petri disk. An indication of the degree of activity of the fungicidal compound alone or in combination with the products according to invention is the diameter of the corona infected by the fungus. The activity of the additive according to the invention is shown in the following Table I:

TABLE I

| | Diameter of the infected corona in mm | | | | | | | | |
|---|---|---|---|---|---|---|---|---|---|
| | 54 | 54 | 35 | 30 | 30 | 40 | 58 | 70 | 80 |
| Concentration of N-acetyl-ethanolamine | 0.003 | 0.01 | 0.03 | 0.1 | 0.3 | 1 | 3 | 10 | 30 |

TABLE I-continued

| | Diameter of the infected corona in mm | | | | | | | |
|---|---|---|---|---|---|---|---|---|
| | 54 | 54 | 35 | 30 | 30 | 40 | 58 | 70 | 80 |
| in ppm | | | | | | | | |

Since the fungicide may only be active by an uptake of the active agent into the fungus cells, the variable activity of the fungicide shows the change in the rate of transportation of the fungicide through the cell membrane of the fungus. This means that by the addition of N-acetylethanolamine in small amounts there is no increase in fungicide transport through the fungus cell membrane, at means amounts there is a substantial increase of the permeability of the cell wall and, thus, fungicidal activity, and at high amounts there is a decrease of the permeablity of the cell membrane or of the rate of transportation of the active agent through the cell membrane.

In a further test, human cancer cells which are kept in culture (so-called KB - cells) are treated with radioactivity marked thymidine and methionine in combination with varying amounts of N-acetylethanol- amine. The cells are separated from the substrate and the amount of the absorbed thymidine and methionine is determined.

The determined values show how the rate of transportation of these two substances through the cell membrane into the cell is influenced in relation to the concentration of the added N-acetylethanolamine:

| Concentration of N-acetylethanolamine | Uptake into the cell in % | |
|---|---|---|
| | Methionine | Thymidine |
| 0 μmole | 0 | 0 |
| 0.1 μmole | +19 | +20 |
| 1 μmole | −42 | −37 |
| 10 μmole | −77 | −62 |

As follows from the above table, small amounts of N-acetylethanolamine positively influence the rate of transportation through the cell membrane while increased amounts decrease the uptake of the two compounds.

The compounds of the formula $$R^1-CO-NH-R^2$$

wherein $R^1$ and $R^2$ have the above given meaning, may be used in accordance to the present invention in all instances where the cells are open to a direct treatment of the development and/or the metabolism of which is to be influenced and modulated.

This treatment may be with these cell modulators alone (f.i. where nutritive agents are available by the natural surrounding) or in combination with active agents or nutritive agents. Active agents may be drugs or various plant protective agents (herbicides or, in particular and most preferred, fungicides). Nutritive agents may be trace elements and compounds, which are necessary for cell nutrition.

Thus, the compounds of the above formula may be used, generally expressed, to influence:
the activity of plant protective agents,
the activity of fertilizers,
the uptake of natural nutritive agents from the soil and atmosphere, with the increase of plant growth,
the growth of microorganisms and yeasts and, thus, of fementation processes,
the activity of antimycotica against human pathogenic germs.

Particularly preferred is the combination of the acid amides $R^1-CO-NH-R^2$ with known fungicides or fertilizers. Most preferred is the combination of the acid amides $R^1-CO-NH-R^2$ with known fungicides.

In the new products according to the invention to treat plants, the N-hydroxyalkyl alkanoic acid amides contained therein increase the effectivity of the fungicides contained therein and combined therewith while the N-hydroxyalkylalkanoic amides themselves do not produce their own fungicidal activity.

Preferably, there may be used as N-hydroxyalkylalkanoic acid amides: N-(2-hydroxyethyl)-, N-(2-acetoxyethyl)-, N-(2-hydroxypropyl)- or N-(3-hydroxypropyl-alkanoic acid amides of acetic acid. Particularly preferred is N-(2-hydroxyethyl)-acetamide and N-methylacetamide each, alone or in admixture thereof in weight proportion of 1:10 to 10:1.

The weight proportion between the active agent, most preferred the fungicidally active agent, and the N-hydroxyalkyl alkanoic acid amide is between 1:0.1 to 1:6. This weight proportion is dependent upon the amount of active agent and, most preferred, the fungicide to be applied. Thus, with an amount of 0.5 to 1.5 kg of active agent, most preferred of fungicide, per hectar (=10000 m²) the weight proportion between the active agent and, most preferred the fungicidally active compound, and the N-hydroxyalkyl alkanoic acid amide is 1:0.1 to 1:2.

With an amount up to 0.5 kg of the active agent—and most preferred of the fungicidally active component—per hectar, the weight proportion of the active agent—most preferred of the fungicidally active component—to N-hydroxyalkyl alkanoic acid amide is 1:1 to 1:6.

As the most preferred fungicidally active agent there may be used any fungicidally active agent, such as the known fungicides of the following groups:

a) Aromatic nitro derivatives of the general Formula II

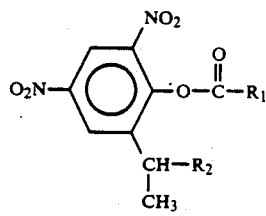

wherein
$R_2$ is $C_{2-4}$-alkenyl or branched alkoxy in particular $C_{1-4}$-alkoxy and
$R_2$ is $C_{2-6}$-alkyl.

The compounds of Formual II are known compounds. Examples are:
2,4-Dinitro-6-(2-butyl)-phenyl-3',3'-dimethylacrylic acid ester (generic name: Binapacryl),
2,4-Dinitro-6-(2-butyl)phenylisopropyloxycarbonic acid ester (generic name: Dinobuton),
2,4-Dinitro-6-(2-octyl)phenylcrotonic acid ester (generic name: Dinocap), b) Chlorobenzene derivatives of the general Formula III

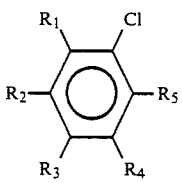

wherein
R₁ is Cl or H;
R₂ is Cl, —OCH₃ or H;
R₃ is Cl or —CN;
R₄ is Cl or H and
R₅ is —CH, —OCH₃ or —NO₂.

The compunds of Formula III are known compounds. Useful examples are for instance:
hexacholorbenzene, pentachloronitrobenzene (generic name: Quintozen), 1,3-dicyan-2,4-2,4,5,6-tetrachlorobenzene (generic name: Chlorothalonil), 1,4-dichloro-2,5-dimethoxy-benzene (generic name: Chloroneb), 1,3,5,6-tetrachloronitrobenzene (generic name: Tecenazen).

c) Phthalic acid derivatives of the general Formula IV

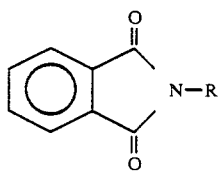

wherein
R is alkylthio, in particular C₁₋₄-alkylthio, in particular methylthio, haloalkyl, in particular C₁₋₄-haloalkyl, in particular trichloromethyl or thionophosphoryl.

The compounds of Formula IV are known compounds. Examples are:
Ditalimphos /N-(diethoxy-thiophosphoryl)-phthalimide/, Captan /N-(trichloromethylthio)-4-cyclohexen-1.2-dicarboximide/, Folpet /N-(trichloromethylthio)-phthalimide/, Captafol /N-(1.1.2.2-tetrachloroethyltho)-phthalimide/, Chlorothalonil or nitrothal.

d) A fungicide of the series of thiocarbamates:
Ferbam,
Mancozeb,
Maneb=Manganese-ethylene-1.2-bis-dithiocarbamate,
Metiram,
Methylmetiram,
Propamocarb,
Propined=Zinc-propylene-1.2-bis-diethiocarbamidate,
Prothiocarb=S-ethyl-N-(3-dimethylaminopropyl)-thiocarbamate-hydrochloride,
Vonozeb
Zineb=Zinc-ethylene-1.2-bis-dithiocarbamidate,
Zinoc=N-methyl-bis-(zinc-ethylene-bis-dithiocarbamidate,
Ziram=Zinc-diemthyldithiocarbamate,
Thiram=Bis-(dimethylthiocarbamoyl)-disulfide.

e) A fungicide of the group of the benzimidazoles such as:
Benomyl=1-(n-butylcarbamoyl)-2-methoxycarbonyl-amino)-benzimidazol,
Carbendazin=2-(methoxycarbonyl-amino)-benzimidazol,
Fuberidazol=2-(2-furyl)-benzimidazol, Rabenazol,
Thisbendazol=2-(4-thiazolyl)-benzimidazol.

f) A fungiciide of the group of the anilin derivatives such
Benodanil=2-jodobenzoic acid anilide,
Carboxin=2.3-dihydro-2-methyl-1.4-oxathiion-3-carboxanilide,
Chloroaniformethan=N-formyl-N'-3.4-dichlorophenyltrichlorophenyltrichloroacetataldehyd-animal,
Dichloran=2.6-dichloro-4-nitroaniline, Fenfuram, Furaloxyl, methfuroxam,
Oxycarboxin=2.3-dihydro-6-methyl-1.4-oxathiion-5-carboxylic acid anilide-S-dioxide.

g) Further useful fungicides:
Thiophanat=1.2-bis-(3-methoxycarbonyl-2-thioureide)-benzene,
Dodemorph=N-Tridecyl-2.6-dimethylmorpholine,
Anilazin=2.4-dichloro-6-(o-chloroanilino)-S-triazine,
Buprimat=2-ethylamino-4-dimethylamidosulfonat-5-butyl-6-methyl-pyrimidine, Cetactaelat,
Chinomethionat=6-methylchinoxalin-2.3-dithio-cyclocarbonate, Chlormethionat,
Dichlofluanid=N,N-dimethyl-N'-phenyl-N'-fluoro-dichloro-methylthio-sulfamide,
Dimethirimol=5n-butyl-2-dimethylamino-4-hydroxy-6-methyl-pyrimidine,
Dithianon=2.3-dicyano-1.4-dithia-anthrachinone,
Dodin=n-dodeylquanidin-acetate,
Ethirimol=2-ethylamino-5b-butyl-4-hydroxy-6-methyl-pyrimidine,
Fenaminsulf=p-dimethylaminobenzoldisulfonat-Na-salt,
Fenarimol=-(2-chlorophenyl)- -(4-chlorophenyl)-5-pyrimidin-methanol,
Iprodion=1-isopropylcarbamoyl-3-(3.5-dichlorophenyl)-hydantion,
Procymidon=N-(3.5-dichlorophenyl)-1.2 dimethyl-cyclopropan-1.2-dicarboximide,
Pyrazophos=0.0-diethyl-0-(5-methyl-6-ethyloxycarbonyl-pyrazolo-/1.5-a/-pyrimidin-2-yl)-thiophosphate,
Tolylfluanid=N,N-dimethyl-N'-(4-methylphenyl)-N'-fluorodichloromethylthio-sulfamide,
Triadimefon=1-(4-chlorophenoxy)-3.3-dimethyl-1-(1.2.4-triazol-1-yl)-2-butanone, Triadimenol,
Triforin=1,4-di-(2.2.2-trichloro-1-formamidocityl)-piperazine,
Viunclozolin=3-(3'5'-dichlorophenyl)-5-methyl-vinyl-1.3-oxazolidin-2.4-dione.

The above fungicides are used alone or together with other fungicides, are used in combination with an N-hydroxyalkyl alkanoic acid amide in accordance with the present invention. The new products to treat plants may be used for fighting the most varying deseases caused by the following fungi : By the fungus *Alternaria solani* in potatoes or tomato plants; Botrytis putridity in strawberrys and grape by the fungus *Botrytis cinerea*; the dying of elm trees by the fungus Ceratocystis ulmi; in grapes by the fungus Cercospora beticola; in bananas by the fungus Cercispora musae; scruf in peach trees by the fungus Cladosporium carphphilum; in cucumbers by the fungus Cladosporium cucumerinum; in tomatos by the fungus Cladosproium fulvum; in stone fruits by the fungus *Clasterosporium carphophilum*; in rye by the fungus *Claviceps purpurea*; in cherry trees by the fungus *Collectotrichum lindemuthianum*; in rose bushes by the fungus *Diploccarpon rosae* or *Marssonima rosae*; real mildew in cucumbers by the fungus *Erysphe cichoracearum*; mildew of corn by the fungus *Erysiphe graminis*; in tea plants by the fungus *Exobasidium vexans*; in tomatos by the fungus *Fusarium oxysporum*; Panama diseases of bananas, in corn plants by the fungus *Furasium nivale*; in cherry trees by the fungus *Venturia cerasi*; in pear trees by the fungus *Bymnosporangium sabinae*; in barley by the fungus *Helminthosprorium gramineum*; in coffee trees by the fungus *Hemileia vastatrix*; in plants by the fungus *Mycena citricolor*; in tobacco plants by the fungus *Peronospora tabacina*; in beets by the fungus *Phoma betae*; putridity in apples, potatos, tomatos by the fungus *Phytophtora infestans*: Brusone disease in rice by the fungus *Pyricularia oryzae*; apple mildew by the fungus *Podosphaera leucotricha*; mildew of hop plants by the fungus *Sphaerotheca humuli*; mildew of rose bushes by the fungus *Sphaerotheca pannosa*; in potatos by the fungus *Synchytrium endobioticum*; in wheat by the fungus *Tilletia caries*; in oat plants by the fungus *Ustilago avenae*; in barley plants by the fungus *Ustilago nuda*; in wheat plants by the fungus *Ustilago tritici* and other known fungi.

The new products to treat plants according to the present invention are produced by known methods by mixing the components and, possibly further additive agenst such as fillers, carriers, diluents, surfact active agents, stabilizers, diluents, anti-freezing agents or the like.

Alternatively it is possible to add the above membrane modulating agents according to the invention to the fungicidal trade products only in the preparation of the spraying solutions (so-called tank-mix procdure).

The new agents to treat plants according to the present invention may be in liquid form or in solid form, for instance as dusting products, granulates, spraying agents, aerosols, emulsions or solutions, as fungicidal compound to treat the leaf, as disinfectant or as fungicidal product to treat the soil.

Preferred fungicides in the new products to treat plants are:
Triadimefon (1-(4-chlorophenoxy)-3.3-dimethyl-1-(1.2.4-triazol-1-yl)-2-butanon,
Fenarimol ($\alpha$-(2-chlorophenyl)-$\alpha$-(4-chlorophenyl)-5-pyrimidinmethanol,
Folpet (N-(trichloromethylthio)-phthalimide),
Dichlofluanid (N,N-dimethyl-N'-phenyl-N'-fluorodichloromethylthio-sulfamide),
Benomyl (1-(n-butylcarbamoyl)-2-methoxycarbonylamino)-benzimidazol),
Mancozeb.

Particularly preferred are those products to treat the plants which are composed of the fungicides Triadimefon, Fenarimol, Folpet, Chlorothalonil, Triadimenol, Procymidon, Carbendazim, Propamocarb, Benomyl, Mancozeb, Captan or Dichlofluanid with N-hydroxyethylacetamide.

With the new fungicidally active products there may be treated in particular disease caused by the fungi *Botrytis cinerea* in wine yards and beans, *Erysiphe graminis* in cereal plants and *Venturia inaequalis* in apple trees.

The compounds of the above formula $R^1$—CO—NH—$R^2$ may be further combined in accordance with the invention with known herbicides 1. phenoxy carboxylic acid derivatives corresponding to the following general formula V

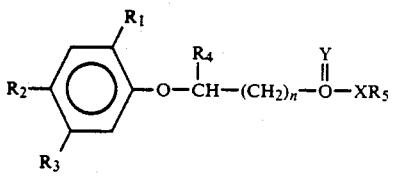

in which
a) $R_1$, $R_2$ and $R_3$ may be the same or different and represent H, $CH_3$ or halogen, particularly chlorine, with the proviso that at most two radicals represent H, $R_4$ represents H or $CH_3$, n=0-2, Y=O or S, X=O, NH or S, $R_5$—where X=O—represents H, linear or branched $C_1$-$C_{12}$-alkyl, hydroxyalkyl, such as hydroxyethyl, trifluoromethyl-phenyl or alkali or alkaline-earth cations and, in particular, ammonium cations, i.e. salts of the acids with ammonia or organic amines, such as for example hydroxyethylamine or trihydroxyethylamine, or $R_5$—where X=NH—represents H, $NH_2$, phenyl optionally substituted by 1 to 3 halogen atoms, heterocyclic groups such as, 2-thiazolyl, or
b) $R_1$ and $R_3$ represent H, $R_2$ represents

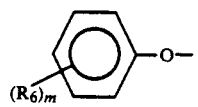

$R_4$ and $R_5$ have the same meaning as in a) $R_6$ represents $CH_3$, halogen or trifluoromethyl and M=1.3.

The substances are known compounds which are described in the following patents: U.S. Pat. No. 3,352,897, U.S. Pat. No. 2,390,942, DE-PS No. 915,876, DE-AS No. 11 15 515, FR-PS No. 1,222,916, GB-PS No. 822,199, GB-PS No. 573,477, DE-AS No. 11 24 296, GB-PS No. 1,041,982, CA-PS No. 570,065, U.S. Pat. No. 3,076,025.

The following are examples of compounds corresponding to general formula V: 4-chlorphenoxyacetic acid-N,O-methylamide, 2,4-dichlorophenoxyacetic acid, 2,4-dichlorophenoxyacetic acid hydrazide, 2-methyl-4-chlorophenoxyacetic acid hydrazide, 2-chloro-4-fluorophenoxyacetic acid, 2-chloro-4-fluorophenoxyacetic acid, butyl ester, 4-chloro-2-methyl phenoxyacetic acid, 4-chloro-2-methylphenoxythioacetic acid, N-(2-chlorophenyl)-4-chloro-2-methylphenoxyacetamide, N-(3-trifluoromethyl-phenyl)-2,4-dimethyl phenoxy acetamide, 2,4-dimethylphenoxyacetic acid, 2,4,5-trichlorophenoxyacetic acid, 2-(4-chlorophenoxy)propionic acid, 2-(2-methylphenoxy)-propionic acid, 2-(2-methyl-4-chlorophenoxy)-propionic acid (mecoprop), 2-(2-methyl-4-chlorophenoxy)-propionic acid-N-(trifluoromethylphenyl)-amide, 2-(2,4,5-trichlorophenoxy)-propionic acid (fenoprop), 2-[4-(2,4-dichlorophenoxy)-phenoxy]-propionic acid, 2-[4-(4-chlorophenoxy)-phenoxy]-propionic acid, 4-(4-chlorophenoxy)-butyric acid, 4-(4-chloro-2-methylphenoxy)butyric acid (MCPB), 4-(2,4,5-trichlorophenoxy)butyric acid, but more particularly 2,4-dichlorophenoxyacetic acid (2,4-D) and its salts and esters, such as the sodium or ammonium salts, or salts with ethanolamine or triethanolamine, 2,4,5-trichlorophenoxyacetic acid (2,4,5-triphenac) and its salts and esters, which may be used in combination as a selective leaf herbicide for controlling dicotyledonous weeds such as, for example, knotgrasses, camomile and thistle in cereal crops, corn, rice, sugar cane or grassland.

2. Urea derivatives corresponding to the following general formula VI

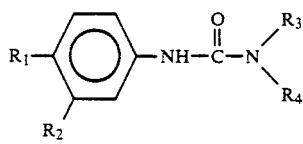

in which $R_1$ and $R_2$ represents H, linear or branched $C_1$-$C_4$-alkyl, cycloalkyl, halogen, particularly chlorine, trifluoromethyl, nitro, alkoxy, optionally halogen-substituted phenoxy, chlorodifluoromethylthio at most one of the groups $R_1$ and $R_2$ representing H, $R_3$ represents H, $CH_3$, $C_2H_5$, $R_4$ represents H, cycloalkyl, $C_1$-$C_4$-alkyl, $C_4$-alkynyl, methoxy.

The compounds corresponding to general formula VI are known compounds and are described in the following patents: U.S. Pat. No. 2,655,447, DE-PS No. 935,165, DE-PS No. 951,181, DE-OS No. 20 39 041, DE-OS No. 21 07 774, DE-OS No. 21 37 992, DE-OS No. 20 50 776, DE-PS No. 968,273, DE-OS No. 19 05 598.

The following are examples of compounds corresponding to formula VI 3-phenyl-1,1-dimethylurea (fenuron), 1-(2-methyl-cyclohexyl)-3-phenylurea (siduron), 3-(4-isopropyl-phenyl)-1,1-dimethyl urea (isoproturon), 3-(4-t-butyl-phenyl)-1,1-dimethylurea, 3-(4-chloro-phenyl)-1,1-dimethylurea (monuron), 3-(3,4-dichloro-phenyl)-1,1-dimethylurea (diuron), N-(3,4-dichloro-phenyl)-N-diethylurea, 1-n-butyl-1-methyl-3-(3,4-dichlorophenyl)-urea (neburon), N-(3-trifluoromethylphenyl)-1,1-dimethylurea (fluometuron), 3-(3-chloro-4-methylphenyl)-1,1-dimethylurea (chlortoluron), 3-(4-chlorophenyl)-1-methyl-1-(1-methyl-prop-2-ynyl)-urea (buturon), 1-(α,α-dimethylbenzyl)-3-(4-methylphenyl)-urea, 3-(3-chloro-4-methoxyphenyl)-1,1-dimethylurea (metoxuron), 3-[(4-chlorophenoxy)-phenyl]-1,1-dimethylurea (chloroxuran), 3-(4-chlorophenyl)-1-methoxy-1-methylurea (monolinuron), 3-(4-bromophenyl)-1-methoxy-1-methylurea (metobromuron), 3-(3,4-dichlorophenyl)-1-methoxy-1-methylurea (linuron), 3-(3-chloro-4-bromophenyl)-1-methoxy-1-methylurea (chlorbromuron), 3-[3-chloro-4-chlorodifluoromethylthio)phenyl]-1,1-dimethylurea (thiochloromethyl), but more particularly 3-(4-isopropyl-phenyl)-1,1-dimethylurea (isoproturon) or 3-(3,4-diichlorophenyl)-1-methoxy-1-methylurea (linuron) which may be used in combination as selective pre-emergence and post-emergence herbicides for controlling wild grasses such as, for example Alopercurus myosuroides, Apera spicaventi, Poa spp., Avena fatura, and annual weeds in winter wheat, winter barley and rye or weeds in vegetable plantations, orchards and vineyards.

3. Organic phosphorus and arsenic compounds, such as O,O-diisopropyl-S-[2-(phenylsulfonylamino)-ethyl]-dithiophosphate (bensulide), N-(phosphonomethyl)-glycine (glyphosate), salts of ethyl carbamoyl phosphoric acid, the disodium salt of methylarsenic acid, dimethylarsinic acid.

4. Alcohols and aldehydes, such as ethyl xanthogene disulfide, alcyl alcohol, acrolein.

5. Substituted alkane carboxylic acids such as, for example, monochlloroacetic acid, N,N-diallyl-chloroacetamide (allidochlor), 2,3,6-trichloro-phenylacetic acid (chlorfenac), benzamido-oxyacetic acid (benzadox), 4-chloro-2-oxobenzothiazolin-3-ylacetic acid (benazolin), N,N-dimethyl-2,2-diphenyl acetamide (diphenamid), trichloroacetic acid, ethylene glycol-bis-(trichloroacetate), 2-chloro-3-(4-chlorophenyl)-propionic acid methyl ester (chlorophenprop), 2,2-dichloropropionic acid, β-naphthyloxy-acetic acid methyl ester, N,N-dimethyl-2-(1-naphthyloxy)propionamide (napromid).

6. Aromatic carboxylic acid derivatives corresponding to the following general formula VII

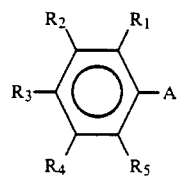

in which $R_1$, to $R_5$ may be the same or different and represent H, halogen, $NH_2$, methoxy, —$COOCH_3$, —$COONH$-naphthyl, $NO_2$, at most four groups representing H, A represents —$COOR_6$, —$CONR_7R_8$, —$CSNR_7R_8$, —$COSR_6$, —CN, $R_6$ represents H, alkali, alkaline-earth, alkyl, hydroxy alkyl, $R_7$ represents H, alkyl, $R_8$ represents H, alkyl, hydroxyalkyl, benzyl except those compounds of formula VII wherein $R_1$ and $R_3$ both are nitrogen, $R_2$ and $R_4$ both are hydrogen, $R_5$ is branched alkyl and $R_6$ is —CO—$C_{2-4}$-alkenyl or branched alkoxy.

The compounds corresponding to general formula VII are known compounds and are described for example in the following patents: U.S. Pat. No. 027,248, GB-PS No. 987,253, U.S. Pat. No. 3,534,098, U.S. Pat. No. 3,013,054, U.S. Pat. No. 3,081,162, U.S. Pat. No. 2,923,634 and GB-PS No. 671,153.

The following are examples of compounds corresponding to formula VII:

2,6-dichlroobenzonitrile (dichlorbenil),
2,6-dichlorobenzoic acid thioamide (chlorthiamid),
N-(1,1-dimethyl-2-propynyl)-3,5-dichlorobenzamide (propyzamid),
3-amino-2,5-dichlorobenzoic acid (chloramben),
3,6-dichloro-2-methoxybenzoic acid (dicamba),
2,3,6-trichlorobenzoic acid,
dimethyl-2,3,5,6-tetrachloroterephthalate (chlorthal),
N-(1-naphthyl)-phthalamidic acid (naptalam).

7. Phenol derivatives corresponding to the following general formula VIII

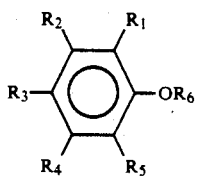

VIII in which

R$_1$ to R$_5$ may be the same or different and represent H, NO$_2$, linear or branched C$_1$-C$_4$-alkyl, halogen, nitrile, trifluoromethyl, at most four groups representing H and R$_6$ represents H, —COCH$_3$, —CSOalkyl, —COCH$_2$—Cl, —COOalkyl, —N=CH—aryl, phenyl optionally substituted by trifluoromethyl, nitro, alkyl, NH$_2$, alkoxy, halogen, except those compounds wherein R$_1$ is chlorine, R$_2$ is chlorine or hydrogen, R$_3$ is chlorine, methoxy or hydrogen, R$_4$ is chlorine or nitril, R$_5$ is chlorine or hydrogen and A is nitril, methoxy or nitro.

The compounds corresponding to general formula VIII are known compounds and are described in the following patents: GB-PS No. 1,067,031, U.S. Pat. No. 2,192,197, GB-PS No. 1,096,037, DE-PS No. 1,088,757, U.S. Pat. No. 3,080,225, U.S. Pat. No. 3,652,645, DE-OS No. 14 93 512.

The following are examples of compounds corresponding to general formula VIII:
3,5-dibromo-4-hydroxybenzonitrile (bromoxynil),
4-hydroxy-3,5-diiodobenzonitrile (ioxynil),
6-methyl-2,4-dinitrophenol (DNOC),
2-sec-butyl-4,6-dinitrophenol (dinoseb),
3,5-dibromo-4-hydroxy benzaldehyde-O-(2,4-dinitrophenyl)oxime (bromofenoxin),
2-sec-butyl-4,6-dinitrophenyl acetate (dinosebactat),
2,4-dichlorophenyl-4'-nitrophenyl ether (nitrofen),
5-(2,4-dichlorophenoxy)-2-nitrobenzoic acid methyl ester (bifenox),
2,4'-dinitro-4-trifluoromethyl diphenyl ether (fluorodifen), pentachlorophenol (PCP),
2,4-dinitro-3-methyl-6-tert-butylphenyl acetate,
2,4-dinitro-6-sec-amylphenol,
2,4,6-trichloro-4'-nitrodiphenyl ether,
3-methyl-4'-nitrodiphenyl ether,
2,4'-dinitro-4-trifluoromethyl diphenyl ether,
2,4-dichlorophenyl-3'-methoxy-4'-nitrophenyl ether,
5-(2-chloro-2-α,α-trifluo-p-tolylox)-2-nitrobenzoic acid sodium salt(Acifluorfin), but especially 2,4-dinitro-6-methyl phenol which may be used in combination for controlling seeds weeds such as, for example, chickweed, goose grass, camomile, knot-grass, speedwell, dead nettle and corn marigold in cereal crops, corn or vineyards, optionally even in conjunction with a hormone herbicide, or pentachlorophenol or 2,4,6-trichlorophenyl-4'-nitrophenyl ether, particularly for controlling barnyard grass and bullrushes in paddy fields.

8. Anilines corresponding to the following general formula IX

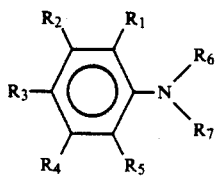

IX in which

R$_1$ represents H, C$_1$-C$_3$-alkyl or nitro, R$_2$ represents H, halogen or NH$_2$, R$_3$ represents C$_1$-C$_3$-alkyl, H, —CF$_3$, —SO$_2$CH$_3$ or —SO$_2$NH$_2$, R$_4$ represents H or C$_1$-C$_3$-alkyl, R$_5$ represents H, NO$_2$ or C$_1$-C$_3$-alkyl, R$_6$ represents H, C$_1$-C$_3$-alkyl, C$_1$-C$_4$-alkoxymethyl or cyclopropylmethyl and R$_7$ represents linear or branched C$_1$-C$_5$-alkyl or linear or branched C$_1$-C$_7$-acyl.

The compounds corresponding to formula IX are known compounds and are described in the following patents: U.S. Pat. No. 3,257,190, U.S. Pat. No. 3,546,295, U.S. Pat. No. 2,863,752, DE-AS No. 11 66 547, U.S. Pat. No. 3,020,142, DE-AS No. 10 39 779, U.S. Pat. No. 3,442,945, GB-PS No. 1,164,160, DE-OS No. 22 41 408.

The following are examples of compounds corresponding to formula IX:
N,N-dipropyl-2,6-dinitro-4-trifluoromethylanilide (trifluralin),
N-ethyl-N-butyl-2,6-dinitro-4-trifluoromethylaniline (benfluralin),
N-cyclopropyl-methyl-N-propyl-2,6-dinitro-4-trifluoromethylaniline (profluralin),
3-diethylamino-2,4-dinitro-6-trifluoromethylaniline (dinitramine),
N-(1-ethylpropyl)-3,4-dimethyl-2,6-dinitroaniline (penoxyn),
N,N-dipropyl-4-methylsulfonyl-2,6-dinitroaniline (nitralin),
4-(dipropylamino)-3,5-dinitrobenzenesulfonamide (oryzalin),
N,N-dipropyl-2,6-dinitro-4-isopropylaniline (isopropalin),
N-isopropyl-α-chloracetanilide (propachlor),
α, α-dimethyl valeryl-4-chloroanilide (monalid),
N-(3-chloro-4-methylphenyl)-2-methylvaleramide (pentanochlor),
propionic acid-3,4-dichloroanilide (propanil),
2',6'-diethyl-N-(methoxymethyl)-2-chloroacetanilide (alachlor),
2',6'-diethyl-N-(butoxymethyl)-2-chloroacetanilide (butachlor),
2-(N-benzoyl-3,4-dichloroanilino)-propionic acid ethyl ester, but especially
3',4'-dichloropropionanilide (propanil).

9. Carbamates corresponding to the following general formula X

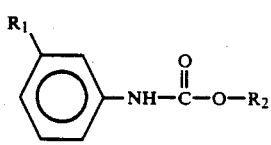

X in which

R$_1$ represents H, halogen, particularly chlorine, CH$_3$ or NHCOOC$_2$H$_5$ and R$_2$ represents H, linear or branched $C_1$-$C_4$-alkyl, haloalkyl, haloalkynyl, alkynyl, 3-(methoxycarbamoyl)-phenyl.

The compounds corresponding to formula X are known compounds and are described for example in the following patents: U.S. Pat. No. 3,334,989, DE-AS No. 11 59 432, DE-AS No. 11 88 588, U.S. Pat. No. 3,150,179, GB-PS No. 574,995, U.S. Pat. No. 2,695,226, DE-OS No. 15 67 151.

The following are examples of compounds corresponding to formula X:
isopropyl-N-phenylcarbamate (propham),
2 phenylcarbamoyloxy-N-ethylpropionamide (carbetamide),
isopropyl-N-(3-chlorophenyl)-carbamate (chlorpropham),
4-chloro-2-butynyl-N-(3-chlorophenyl)-carbamate (barban),
1-methylpropargyl-N-(3-chlorophenyl)-carbamate (chlorbufam),
methyl-N-(4-aminobenzene-sulfonyl)-carbamate (asulam),
2,6-di-tert.-butyl-4-methylphenyl-N-methylcarbamate (terbucarb),
3-methoxycarbonylaminophenyl-N-(3-methylphenyl)-carbamate (phenmedipham),
3-ethoxycarbonylaminophenyl-N-phenylcarbamate (desmedipham) but especially isopropyl-N-phenylcarbamate,
3-methoxy carbonylamino-phenyl-N-(3-methylphenyl)-carbamate or
3-ethoxycarbonylamino-phenyl-N-phenyl carbamate.

10. Triazines corresponding to the following general formula XI

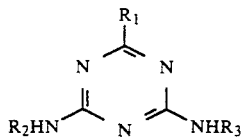

XI in which
$R_1$ represents halogen, particularly chlorine, methylthio or methoxy, and $R_2$ and $R_3$ represent linear or branched $C_1$-$C_4$-alkyl optionally substituted by a nitrile group or azole group.

The compounds corresponding to formula XI are known compounds and are described for example in the following patents: DE-OS No. 14 42 733, CH-PS No. 329,277, CH-PS No. 337,019, DE-AS No. 16 70 528, DE-AS No. 11 86 070.

The following are example of compounds corresponding to formula XI.
2-azido-4-methylthio-6-isopropylamino-1,3,3-triazine (aziprotryn),
2,4-bis-(ethylamino)-6-chloro-1,3,5-triazine (simazin),
2-ethylamino-4-chloro-6-isopropylamino-1,3,5-triazine (atrazine),
2-methylamino-4-methylthio-6-isopropylamino-1,3,5-triazine (desmetryne),
2-(4-ethylamino-6-chloro-1,3,5-triazin-2-ylamino)-2-methylpropionitrile (cyanzine),
2-ethylamino-4-tert.-butylamino-6-chloro-1,3,5-triazine (terbutylazin),
2-chloro-4,6-bis-(isopropylamino)-1,3,5-triazine (propazin),
2-ethylamino-4-methylthio-6-isopropylamino-1,3,5-triazine (ametryne),
2-ethylamino-4-sec.-butylamino-6-methoxy-1,3,5-triazine (secbumeton),
2-ethylamino-4-tert.-butylamino-6-methoxy-1,3,5-triazine (terbumeton),
2-methoxy-4,6-bis-(isopropylamino)-1,3,5-triazine (prometon),
2-ethylamino-4-tert.-butylamino-6-methylthio-1,3,5-triazine (terbutryne),
2-methylthio-4,6-bis(isopropylamino)-1,3,5-triazine (prometryn),
2-(3-methoxypropylamino)-4-methylthio-6-isopropylamino-1,3,5-triazine (methoprotryne), but especially 2-(4-ethylamino-6-chloro-1,3,5-triazin-2-ylamino-)-2-methylpropionitrile).

11. Triazinones corresponding to the following general formula XII

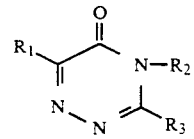

XII in which
$R_1$ represents alkyl, substituted aryl or a cycloaliphatic radical, $R_2$ represents NH2, —NH-alkyl or N=CH-alkyl and $R_3$ represents C1-C4-alkyl, alkoxy or alkylthio.

The compounds corresponding to formula XII are known compounds and are described, for example in the following patents: U.S. Pat. No. 3,671,523, DE-OS No. 24 07 144 and U.S. Pat. No. 3,847,914.

The following are examples of compounds corresponding to formula XII.
4-amino-6-tert.-butyl-3-methylthio-1,2,4-triazin-5(4H)-one (metribuzin),
6-tert.-butyl-4-isobutylidene-amino-3-methylthio-1,2,4-triazin-5(4H)-one (isomethiozin), but especially
4-amino-3-methyl-6-phenyl-1,2,4-triazin-5(4H)-one (metamitron).

12. Other herbicides which may be used include,
3,6-epoxycyclohexane-1,2-dicarboxylic acid (endothal),
S-ethyl-N,N-diethylthiocarbamate (ethiolat),
S-ethyl-N,N-hexamethylene thiocarbamate (molinat),
S-ethyl-N,N-dipropyl thiocarbamate (EPTC),
S-ethyl-N-ethyl-N-cyclohexyl thiocarbamate (cyclat),
S-ethyl-N,N-diisobutyl thiocarbamate (butylat),
S-propyl-N,N-dipropyl thiocarbamate (vernolat),
S-propyl-N-ethyl-N-butyl thiocarbamate (pebulat),
2-chloroallyl-N,N-diethyl dithiocarbamate (sulfallat),
S-(2,3,3-trichloroallyl)-N,N-diisopropylthiocarbamate (trillat),
S-(2,3-dichloroallyl)-N,N-diisopropylthiocarbamate (diallat),
S-(4-chlorobenzyl)-N,N-diethylthiocarbamate (benthiocarb),
1,3-dimethyl-1-(5-trifluoromethyl-1,3,4-thiodiazol-2-yl)urea (thiazfluron),
1-(5-ethylsulfonyl-1,3,4-thiadiazol-2-yl)-1,3-dimethyl urea (sulfodiazol), N-isobutyl-2-oxo-1-imidazolidinecarboxamide (isocarbamid),
1-(2-benzothiazolyl)-1,3-dimethyl urea (methabenzthiazuron),
1,1-ethylene-2,2'-dipyridylium dibromide (diquat),
1,1'-dimethyl-4,4'-dipyridylium dichloride (paraquat), Particularly preferred herbicides are those of the above group 1 at page 15 and group 10 at page 25. Most preferred herbicides are Amitrol, Simazin, MCPA, Chloromequatchloride, Ethephon and Acifluorfen-sodium-salt used alone or in combination of several of them as described in the following Examples 1, 2 and 4.

The new herbicidal compositions may be applied by standard methods, for example as soil or leaf herbicides or as systemic herbicides or contact herbicides before or after sowing or after emergence, according to requirements.

The new herbicidal compositions are used primarily for controlling weeds and wild grasses such as, for example,
Alopeurus myosuroides,
Bromus tectorum,
Cyperus rotundus,
Digitaria sanquinalis,
Echinochlora crus galli,
Eleusine indica,
Festuca ovina,
Lolium perenne,
Phleum protense,
Setaria italica,
Poa annua,
Setaria viridis,
Sorghum halepense,
Abutilon theophrasti,
Amaranthus retroflexus,
Anthemis arvensis,
Chenopodium album,
Chrysanthemum segetum,
Convolutuss arvensis,
Agropyron repens,
Apera pica-venti,
Arrhenaterum elastius bulbosum,
Pennisetum clandestinum,
Ischaemum rugosum,
Rottboellia exaltata,
Imperata cylindrica,
Poa trivalis,
Leptochloa filiformis,
Setaria faberii,
Gallium aparine,
Girsium arvense,
Atriplex spp., which hinder or are harmful to the cultivation of useful plants in one-crop systems. Examples of useful plants which may be protected against weeds and wild grasses are oats, barley, rice, millet, wheat, corn, sugar beet, cane sugar, potatoes, soya beans, cotton, tobacco, coffee, fruit, vegetables or vines.

The use of the compounds $R^1$—CO—NH—$R^2$ as membranes modulating substances in accordance with the present invention gives extremely good results also in combination with fertilizers. As main fertilizer or nutritive product there may be used known nitrogen fertilizers, known phosphate fertilizers, known potassium fertilizers or mixtures thereof. Such known nitrogen fertilizers are for instance ammonium sulphate, calcium ammonium nitrate, urea, urea-aldehyde-condensation products, nitrogen magnesium oxide products, ammonium sulphate nitrate, calcium nitrate or calcium cyanimide. Known phosphate fertilizers are for instance superphosphate, doublesuperphosphate, triplesuperphosphate, thomasgrain, thomasphosphate, glowphosphate, rhenaniaphosphate, dicalciumphosphate or crudephosphate. Useful potassium fertilizers are potassium chloride, potassium sulfate, potassium magnesium oxide. Further main nutritive agents may be calcium carbonate such as chalk; calcium oxide, magnesium oxide, kierserit or dolomite. There may be further admixed organic components such as guano, fish-meal, bone meal, lignin or peat. Further, there may be admixed known derivatives of trace elements such as manganese, zinc, iron, copper and molybdenum. For instance, zinc oxide, zinc sulfate, zinc carbonate, copper oxide, molybdenum sulfate and borates of such elements.

The compounds of formula I may be used alone or combined with an active agent or mixtures, which are produced before using them.

Thus, Example 31 illustrates the use of N-hydroxyethylacetamide alone, i.e., without combining it with another active agent. The membrane modulating properties of N-hydroxyethylacetamide is used such that the uptake of naturally occurring nutriments by the plants from the soil is increased. This produces a distinct increase in the weight of green parts in these cultivated plants.

The production and use of products consisting of a combination of usual active agents and one or several compounds of formula I, according to the invention, is described in the following examples. According thereto, the compounds of the general formula I are formulated together with active agents or nutriments as products ready for use. It is however also possible to use two products separately, one of the products containing the active agent or nutriment and the other continuing the compound of formula I. The user of the combination in accordance with the invention may mix both products in the correct proportion immediately before use, for instance in the presence of water, as is usual in agriculture.

In some cases it may be preferable to use several compounds of formula I as membrane modulating agents alone or together with active agents in accordance with the present invention. In this case it is most preferred to use together N-methylacetamide and N-hydroxyethylacetamide in a weight proportion of from 1:10 to 10:1.

The present invention is further directed to a process for producing antibiotics etc. penicillins or cephalosporins by fermentation. In this process known process conditions for such a fermentation process are applied and there is added to the fermentation broth one or several products of the general formula I in a concentration of 5 to 100 μmole/l. By adding a compound according to formula I to the fermentation broth in the above amount there is considerably increased the yield in the desired penicillin compound.

Still furthermore, the present invention is related to a process for microbiological upgrading agricultural waste products by the applicatoion of known process conditoons for such processes with and by adding one or several products according to the general formula I to the fermentation mixture or the like product started from in this process in a concentration of from 0.1:1%, in relation to the solids content of the fermentation mixture.

Still furthermore, the invention is directed to a process for cultivating yeast. Again, known conditions for such processes are applied and, according to the invention, there are added to the nutritive solution one or several products according to the general formula I in a concentration of 5 to 250 μmole/l.

Finally, the invention is directed to a process for combating human pathogenic germs with antimykotic agents. Again, known conditions for such processes are applied and, according to the invention, the antimykotic agent is combined with one or several products according to the general formula I in a concentration of from 0.08 to 0.5%. It is surprising that the effectivity of the antimykotic agent is considerably increased when applying the antimykotic agent in a combination with the cell modulating agents according to the present invention in the above specific amounts or in combination product the amount of antimykotic agent may be decreased while producing the same effect as with the antimykotic agent alone.

The following examples illustrate the products according to the present invention and their use in modulating cell membranes.

EXAMPLE 1

| Amitrol | 38.0% |
|---|---|
| Simazin | 19.5% |
| MCPA | 16.0% |
| N-Hydroxyethylacetamide | 8.0% |
| Siliciumdioxide, highly dispersed | 8.0% |
| Nonylphenolethylenoxide-addition product | 3.0% |
| Lignolsulfonate | 3.0% |
| Kaoline | 4.5% |

The ground active agents were mixed with the various inert auxiliary agents in a mixture for powderous materials in usual manner to result in a sprayying powder.

EXAMPLE 2

| Chlormequatchloride | 305 g |
|---|---|
| Ethephon | 155 g |
| N-Hydroxyethylacetamide | 80 g |
| Water | ad 1000 ml |

The active agents are dissolved in the above sequence in 500 ml of water, N-hydroxyethylacetamide is added and the mixture is finally supplemented to a volume of 1000 ml with water as denoted above by the abbreviation "ad". The mixture is thoroughly mixed.

EXAMPLE 3

Increase of the effectiveness of the plant growth regulating agents chlormequatchloride and ethephone.

The following tests have been effected:

Trays of 20×20 cm are filled with a standard soil material usual for such growth tests. There have been grown a winter corn species in the trays, 60 plants per tray, in a green house. The plants were treated when 8 to 10 cm high. The materials to be tested have been sprayed with a total of 1000 l/ha of solution containing the components given below. The tests have been repeated 4 times in a green house. The trays with the plants concerning the growth have been evaluated 36 days after treatment with the various products.

| Test Product | Average size of the plants in cm |
|---|---|
| No treatment | 45 |
| Trade product with 305 g/l of Chlormequatchloride and 155 g/l of Ethaphone; sprayed at 2.5 l/ha | 39 |
| product according to the invention as described in the above Example 2; sprayed at 0.25 l/ha | 29 |

EXAMPLE 4

| Acifluorfen-sodium-salt | 240 g |
|---|---|
| N-Hydroxyethylacetamide | 100 g |
| Water | ad 1000 ml |

The active agent and N-hydroxyethylacetamide are mixed with water by a short stirring.

EXAMPLE 5

Increase of effectivity of the herbicide Acifluorfen.
The following tests have been carried out:

In trays of 20×20 cm, filled with standard soil, mustard plants were cultivated in a green house. Each tray contained 8 mustard plants. The tests have been repeated 4 times. The plants had been treated in the 2-leaves-state by spraying a volume of 1000 l/ha. The tests were evaluated 6 days after treatment. There has been determined the destruction of the plants. 0% means no herbicidal effect and 100% means total destruction and suppression of plant growth.

| Test product | Effectiveness |
|---|---|
| Trade product (24% active ingredient) with 0.2% | 30% |
| Product according to Example 4 (24% active ingredient) with 0.2% | 55% |

EXAMPLE 6

Combat of weeds in fruit-cultures

A test was run in an apple tree plantation to combat undesired weeds. The test was repeated 4 times. The test was run 1) with a trade product consisting of

| 38% | of Amitrol |
|---|---|
| 19.5% | of Simazin |
| 16% | of MCPA |

2) with the product of the invention according to the above Example 1.

The combat of weeds has been continuously observed from July 15 to October 15 with the following results:

| | Jul. 15 | Aug. 15 | Sept. 15 | Oct. 15 |
|---|---|---|---|---|
| Trade product at 5 kg/ha | 3.0 | 5.0 | 8.0 | 5.0 |
| Trade product at 10 kg/ha | 7.5 | 9.0 | 8.5 | 8.0 |
| Product according to | 7.0 | 9.0 | 9.0 | 8.0 |

-continued

|  | Jul. 15 | Aug. 15 | Sept. 15 | Oct. 15 |
|---|---|---|---|---|
| the invention at 5 kg/ha | | | | |

0 = no result
10 = all weed plants have been destroyed

EXAMPLE 7

| Triadimefon | 25% |
|---|---|
| N-(2-Hydroxyethyl)-acetamide | 25% |
| Sodium salt of an aliphatic sulfonic acid | 2% |
| Kresolformaldehyd-condensation product | 4% |
| Pebble chalk | 24% |
| Synthetic silicic acid | 20% |

In a mixer for powderous materials the liquid hydroxyethylacetamide is added to the synthetic silicic acid. The remaining components are mixed to a powder mixture which again is admixed to the first-mentioned product in usual manner. The resulting mixture again is a powderous product.

EXAMPLE 8

| Chlorothalonil | 40% |
|---|---|
| N-(2-Hydroxyethyl)-propionamide | 30% |
| Polyarylphenolphosphat, neutralized with triethanolamine | 2% |
| Ethyleneglycol | 5% |
| Silicon defoamer | 0.5% |
| Water | ad 100% |

The components are milled in a state in a horizontal pearl mill of the type DYNO-MILL in usual manner to result a suspension concentrate.

EXAMPLE 9

| Fenarimol | 10% |
|---|---|
| N-(2-Hydroxyethyl)-acetamide | 10% |
| 3,5,5-Trimethyl-2-cyclohexan-1-one | 20% |
| Cyclohexanol | 5% |
| Ricinol caster oil, ethoxylated | 5% |
| 2,2-Dimethyl-3-dioxolan-4-methanol | 10% |
| Fatty amine polyglycolether | 5% |
| Glycerol ester, ethoxylated | 15% |
| Triglyceride of saturated fatty acids from plants | 20% |

The Fenarimol is dissolved in the mixture of the liquid components with stirring to result an emulsion concentrate.

EXAMPLE 10

| Diclofluanid | 25% |
|---|---|
| N-(2-Hydroxyethyl)-acetamide | 25% |
| Sodium salt of alkylnaphthalinsulfonic acid | 1.5% |
| Sodium salt of phenolsulfonic acid condensation product | 3.5% |
| Synthetic silicic acid | 20% |
| Kaolin | 25% |

The production of the powder product of Example 10 is carried out as described in the above Example 7.

EXAMPLE 11

| Triadimenol | 25% |
|---|---|

-continued

| N-(2-Hydroxyethyl)-acetamide | 25% |
|---|---|
| Synthetic selicic acide | 20% |
| Diatomeons earth | 22.5% |
| Sodium salt of ligninsulfonic acid | 4% |
| Sodium salt of methylnaphthalinsulphonic acid | 2% |
| Dextrine | 0.5% |
| Dye-stuff | 1% |

The products are mixed in an analogous manner as described in Example 7. This powderous product can be used as a dry treatment for seeds.

EXAMPLE 12

| Procymidon | 35% |
|---|---|
| N-(2-Hydroxyethyl)-acetamide | 15% |
| Sodium salt of alkylbenzolsulfonic acid | 2% |
| Silicic acid-formaldehyd-condensation product | 3% |
| Synthetic silicic acid | 15% |
| Pebble chalk | 30% |

This powderous product is produced as in Example 7.

EXAMPLE 13

| Propamocarb | 40% |
|---|---|
| N-(2-Hydroxy-2-methyl-ethyl)-acetamide | 30% |
| Water | 30% |

This product is obtained by dissolving the various components. This solution is used as wet disinfectant.

EXAMPLE 14

| Benomyl | 25% |
|---|---|
| N-(2-Hydroxyethyl)-acetamide | 25% |
| Sodium salt of methylnaphthalinsulfonic acid | 4% |
| Sodium salt of ligninsulfonic acid | 5% |
| Synthetic silicic acid | 25% |
| Kaolin | 16% |

The product is produced as described in Example 7.

EXAMPLE 15

| Mancozeb | 30% |
|---|---|
| N-(2-Hydroxyethyl)-propionamide | 25% |
| Sodium salt of methylnaphthalinsulfonic acid | 3% |
| Synthetic silicic acid | 20% |
| Sodium salt of ligninsulfonic acid | 4% |
| Kaolin | 18% |

The product is produced as described in Example 7.

EXAMPLE 16

| Triadimefon | 10% |
|---|---|
| N-(2-Hydroxyethyl)-acetamide | 15% |
| Cyclohexanol | 10% |
| Toluol | 10% |
| Tetrahydronaphthalin | 5% |
| Dimethylformamide | 25% |
| Acylpolyglycolether | 25% |

The emulsion concentrate is produced in usual manner.

EXAMPLE 17

| | |
|---|---|
| Captan | 20% |
| N-(2-Hydroxy-2-methyl-ethyl)-propionamide | 20% |
| Nonylphenolethoxylate | 1% |
| Naphthalinformaldehyd-condensate | 2.5% |
| Conservation agent | 0.1% |
| Defoamer | 0.1% |
| Ethyleneglycol | 2% |
| Xanthan gum | 0.2% |
| Water | 54.1% |

The above components are mixed in usual manners to result a suspension concentrate which is used as suspension disinfectant.

EXAMPLE 23.1 to 23.4

| | 23.1 | 23.2 | 23.3 | 23.4 | 23.5 |
|---|---|---|---|---|---|
| Ammonnitrate-urea-solution, 8% N | 300 g | 300 g | 300 g | 300 g | 300 g |
| Superphosphate, concentrated. 8% $P_2O_5$ | 210 g | 210 g | 210 g | 210 g | 210 g |
| Potassium sulphate. 6% $K_2O$ | 130 g | 130 g | 130 g | 130 g | 130 g |
| Iron sulphate | 0.5 g | 0.5 g | 0.5 g | 0.5 g | 0.5 g |
| Copper sulphate | 0.2 g | 0.2 g | 0.2 g | 0.2 g | 0.2 g |
| Borax | 0.5 g | 0.5 g | 0.5 g | 0.5 g | 0.5 g |
| Zinc sulphate | 0.2 g | 0.2 g | 0.2 g | 0.2 g | 0.2 g |
| Magnesium sulphate | 0.5 g | 0.5 g | 0.5 g | 0.5 g | 0.5 g |
| N-Hydroxyethylacetamide | 3.3 g | 16.6 g | — | — | —. |
| N-Methylacetamide | — | — | 3.3 g | 16.6 g | — |
| Water | ad 1.0 l | ad 1.0 l | ad 1.0 l | ad 1.0 l | ad 1.0 l |

The components were formulated according to known procedures to yield a liquid fertilizer product.

| Example 24.1 to 24.10 | | | | | | | | | | |
|---|---|---|---|---|---|---|---|---|---|---|
| | 24.1 | 24.2 | 24.3 | 24.4 | 24.5 | 24.6 | 24.7 | 24.8 | 24.9 | 24.10 |
| Ammonnitrate-urea-solution, 9% N | 330 g | 330 g | 330 g | 330 g | 330 g | 330 g | 330 g | 330 g | 330 g | 330 g |
| Superphosphate, concentrated, 9% $P_2O_5$ | 230 g | 230 g | 230 g | 230 g | 230 g | 230 g | 230 g | 230 g | 230 g | 230 g |
| Potassium sulphate, 7% $K_2O$, water soluble | 150 g | 150 g | 150 g | 150 g | 150 g | 150 g | 150 g | 150 g | 150 g | 150 g |
| Iron sulphate | 0.5 g | 0.5 g | 0.5 g | 0.5 g | 0.5 g | 0.5 g | 0.5 g | 0.5 g | 0.5 g | 0.5 g |
| Copper sulphate | 0.2 g | 0.2 g | 0.2 g | 0.2 g | 0.2 g | 0.2 g | 0.2 g | 0.2 g | 0.2 g | 0.2 g |
| Borax | 0.5 g | 0.5 g | 0.5 g | 0.5 g | 0.5 g | 0.5 g | 0.5 g | 0.5 g | 0.5 g | 0.5 g |
| Zinc sulphate | 0.2 g | 0.2 g | 0.2 g | 0.2 g | 0.2 g | 0.2 g | 0.2 g | 0.2 g | 0.2 g | 0.2 g |
| Magnesium sulphate | 0.5 g | 0.5 g | 0.5 g | 0.5 g | 0.5 g | 0.5 g | 0.5 g | 0.5 g | 0.5 g | 0.5 g |
| N-Hydroxyethylacetamide | 8.3 g | 16.6 g | 33.2 g | 66.4 g | 100 g | — | — | — | — | — |
| N-Methylacetamide | — | — | — | — | — | 8.3 g | 16.6 g | 33.2 g | 64.4 g | 100 g |
| Water | ad 1.0 l | ad 1.0 l | ad 1.0 l | ad 1.0 l | ad 1.0 l | ad 1.0 l | ad 1.0 l | ad 1.0 l | ad 1.0 l | ad 1.0 l | the components are formulated according to known procedure to yield a liquid fertilizer product.

EXAMPLES 25

| | |
|---|---|
| Magnesium oxide | 78.00 g |
| Ammonium sulphate | 5.00 g |
| N-Hydroxyethylacetamide | 5.00 g |
| Borax | 0.10 g |
| Iron sulphate | 0.03 g |
| Copper sulphate | 0.01 g |
| Manganese sulphate | 0.08 g |
| Ammonium molybdate | 0.03 g |
| Zinc sulphate | 0.12 g |
| Kaolin | 3.63 g |
| Linolsulfonate | 3.00 g |
| Siliciumdioxid, highly dispersed | 5.00 g |

The pulverized components are mixed to known procedures to yield a sparying powder.

EXAMPLE 26 the combat of grape peduncle necrosis disease in wine plants.

In a vineyard 10 plants of the species Traminer in each experiment were treated. The treatment was repeated 4 times. One treatment was effected with a trade product containing 78% of magnesium oxide and a second test was carried out with the product of Example 25. The amount of MgO in both products was identical. The degree of effectiveness and showed the following result:

| | |
|---|---|
| Untreated: | 0% |
| Trade product (78% MgO) | 11% |
| Product according to the invention. the above Example 25 | 34% |

EXAMPLE 27

3 lots of a field with lucerne plants divided into lots, each lot measuring 20 m² have been treated a usual leaf fertilizer in suspension form being composed of 30% nitrogen
22% potassium
6% magnesium
0.8 g/l boron as well as other trace elements.

Three different lots of this field have been treated with a mixture of the above fertilizer trade product and the compounds of general formula III, in accordance with the present invention, prepared in a usual tank-mix procedure. The amount of nutriments in all tests have been identical. 18 days later the lucerne plants have been collected and the weight of green material has been determined.

| | Weight of green material in kg (total of 3 lots) |
|---|---|
| 1. Untreated | 95.3 |
| 2. Trade product 2 l/ha | 97.6 |
| 3. Trade product 2 l/ha + N-methylacetamide 0.1 l/ha | 101.1 |
| 4. Trade product 2 l/ha + | 103.2 |

-continued

| | Weight of green material in kg (total of 3 lots) |
|---|---|
| N-methylacetamide 0.2 l/ha | |
| 5. Trade product 2 l/ha + N-acetylethanolamine 0.1 l/ha | 100 |
| 6. Trade product 2 l/ha + N-acetylethanolamine 0.2 l/ha | 103.4 |
| 7. Trade product 2 l/ha + N-acetylethanolamine 0.1 l/ha + N-methylacetamide 0.1 l/ha | 104.2 |

EXAMPLE 28

3 lots were fertilized with a commercial liquid fertilizer being composed of
9% nitrogen
9% phosphorous
7% potassium.

The applied amount was 300 l/ha. Thereafter maize silage was sown.

The fertilizers of the above Examples 23.1 to 23.4 have been applied in the same way and in the same amount, resulting in the identical amount of nutriments in all tests. The amount of membrane modulating agent per area was 1 or, respectively, 5 kg/ha.

Three months after sowing the plants have been harvested and collected and the amount of green material has been determined.

| | Amount of green material kg/60 m$^2$ |
|---|---|
| Product according to the above Example 23.1 | 150.3 |
| Product according to the above Example 23.2 | 158.5 |
| Product according to the above Example 23.3 | 149.7 |
| Product according to the above Example 23.4 | 157.2 |
| Product according to the above Example 23.5 | 144.6 |

EXAMPLE 29

In a usual grass plot, test lots of 1 m$^2$ have been treated as follows:

| Test lot | Fertilizer |
|---|---|
| 1 | 25 ml of a commercial NPK (997)-liquid fertilizer (= Nitrogen 9%-Phophorous 9% Kalium 7% liquid fertilizer) is mixed in 5 l of water |
| 2 | same commercial fertilizer as lot 1 with the admixture of 1 ml of N-acetylethanolamine |
| 3 | the same fertilizer is for test lot 1 with admixture of 1 ml of N-methylacetamide |

For the evaluation of the test lots both the lawn density and the plant height and intensity of the green colour have been determined. Desirably a lawn is as, high and green as possible.

Test Procedure and Evaluation:

3 days after treatment with the fertilizers, the lawn including the test areas has been mowed.
11 days after the treatment the lawn has been evaluated as: untreated <1<2<3
20 days after treatment the fertilizers the lawn has been mowed.
42 days after the treatment the lawn areas have been evaluated as: untreated <1<3<2

At the 43$^{rd}$ day after treatment with the fertilizers the lawn has been mowed.
60 days after the treatment the lawn areas have been evaluated as: untreated, 1, 3<2

EXAMPLE 30

Maize silage plants have been treated in the 3 to 4-leaf state. The test lost had an area of 20 m$^2$ and the tests have been repeated four times with a commercial leaf fertilizer (9% nitrogen, 9% phosphorous, 7% potassium) as well as a combination of this commercial leaf fertilizer with products of general formula I, i.e. products to treat plants in accordance with the invention, as produced in Examples 24.1 to 24.10. 3 months after treatment the plants have been collected and the weight of green material has been determined.

| Leaf fertilizer | Weight of green material in kg of lots of 20 m$^2$ each |
|---|---|
| Commercial product 3 l/ha | 237 |
| Product according to the above Example 24.1 with N-acetylethanolamine | 249 |
| Product according to the above Example 24.2 with N-acetylethanoilamine | 258 |
| Product according to the above Example 24.3 with N-acetylethanolamine | 256 |
| Product according to the above Example 24.4 with N-acetylethanolamine | 257 |
| Product according to the above Example 24.5 with N-acetylethanolamine | 258 |
| Product according to the above Example 24.6 with N-methylacetamide | 261 |
| Product according to the above Example 24.7 with N-methylacetamide | 264 |
| Product according to the above Example 24.8 with N-methylacetamide | 268 |
| Product according to the above Example 24.9 with N-methylacetamide | 261 |
| Product according to the above Example 24.10 with N-methylacetamide | 243 |

EXAMPLE 31

Increase of green material from maize silage. 120 plants in trays of 40×40 cm have been cultivated in a green house at 19° to 20° C. The treated plants had been 10 to 12 cm high. The tests have been repeated four times. In the test, the plants have been sprayed with water containing the test compound in a total liquid of 600 l/ha. 18 days after the treatment the plants have been collected and the weight of the green material has been determined. The result of the test was as follows:

| Amount of N-acetylethanol-amine in g/ha | 0 | 3.2 | 10 | 32 | 100 | 320 | 1000 |
|---|---|---|---|---|---|---|---|
| weight of green material in % over water spraying without N-acetyl-ethanolamine | 100 | 99 | 101 | 100 | 107 | 106 | 116 |

EXAMPLE 32

Improvement of penicillin G production by fermentation.

The precultures of a particular microorganism breed as used in the production of penicillin G is cultivated 3 days at 25° C. in a shaking machine. The cells are isolated and 8 ml of the fungus mycel in saline solution is given to 30 ml of a usual substrate.

In separate tests the same procedure is applied and, in accordance with the invention, there are added the cell modulators in two concentrations to the above described substrate.

The thus produced microorganism cultures are incabated 5 days at 25° C. with shaking.

The suspensions are further processed as usual and analysed to the content in the fermentatively produced antibiotic.

| Test | stiumulated factor |
|---|---|
| without the addition of a cell modulator, i.e. under known commercial condiditons | 0 |
| with the addition of 5 μmole of N-acetylethanolamine | 2 |
| with the addition of 100 μmole of N-acetylethanolamine | 10 |
| with the addition of 5 μmole of N-methylacetylamide | 3 |
| with the addition of 100 μmole of N-methylacetylamide | 8 |

EXAMPLE 33

Improvement of the fermentative processing of the agricultural waste product "Gülle" (semiliquid manure).

20 ml of a commercial product containing microorganism, nutrient for them preservatives etc. for the fermentative processing is added to 1 l of the waste product. By making continuous analysis during the fermentation process it is determined at which time the microorganisms used changed all of the ammonia present in the waste product into nitrates. If all ammonia has been changed into nitrates the fermentation is considered as finished.

In a comparative test, in accordance with the invention, the cell modulators have been added to the fermentation broth together with the commercial product in the beginning of the procedure and the termination of fermentation has been determined in the same way.

| Fermentation broth | Termination of fermentation after time of addition of microorganisms |
|---|---|
| 1. Standard mixture of known known microorganism and known nutriments | 16 hours |
| 2. The same as 1. with the addition of 0.01% of N-acetylethanolamine to the fermentation broth | 12 hour |
| 3. The same as 1. with the addition of 0.01% of N-methylacetamide | 13 hour |

EXAMPLE 34

Improvement of growth of yeast.

Yeast is added in a concentration of 15 mg/ml to a usual substrate containing 42 mmole of KCl. The substrate has a pH of 3.85. The addition of 42 mmole of glucose causes growth of the yeast. In a parallel test there is added to the glucose to be added to the substrate, in accordance with the invention, 25 μmoles of the compounds of general formula I. In all instances the change of the pH value over the time is determined as a measure of yeast growth. Furthermore, the yeast cultivation is tested on its optical density as a further means to determine the degree of yeast growth.

| | pH value | | |
|---|---|---|---|
| Time after glucose addition (minutes) | under usual growth conditions | with the addition of N-acetyl-ethanolamide | with the addition of N-methyl-acetamide |
| 0 | 3.85 | 3.85 | 3.85 |
| 1 | 3.84 | 3.84 | 3.83 |
| 3 | 3.73 | 3.65 | 3.60 |
| 5 | 3.67 | 3.50 | 3.41 |

The evaluation of the optical density of the yeast cultivation broth showed that, when adding an acid amide according to the general formula I in accordance with the invention, the growth speed is improved by 42 and 48% over usual yeast growth speed is improved by 42 and 48% over usual yeast growth conditions.

We claim:

1. Process to improve the activity of an active agent selected from the group consisting of herbicides or fertilizers comprising applying to a plant an aqueous solution containing both an effective amount of the herbicidal or fertilizing active agent and a water-soluble compound of the general formala I $$R^1-CO-NH-R^2$$

wherein
 $R^1$ is methyl or ethyl and
 $R^2$ is 2-hydroxyethyl, the weight proportion of the active agent to the compound of general formula I in the aqueous solution is 1:1 to 1:6.

2. Process according to claim 1, wherein a compound of formula I is used wherein $R^1$ is methyl.

* * * * *

UNITED STATES PATENT AND TRADEMARK OFFICE
CERTIFICATE OF CORRECTION

PATENT NO. : 5,129,950

DATED : July 14, 1992

INVENTOR(S) : Miklos Ghyczy et al.

It is certified that error appears in the above-identified patent and that said Letters Patent is hereby corrected as shown below:

On the title page, Item [54]: Title of the Invention:
" -Propanamide" should be -- Propanamide --.

On the title page, Item [73]: Assignee:
"A Nattermann" should be -- A. Nattermann --.

Column 1, line 5, in the Title, " -Propanamide" should be -- Propanamide --.

Column 1, lines 15 and 16, delete "bactercides" and insert --bactericides--.

Column 1, lines 19 and 20, delete "the activity of these compounds, probably by an influence".

Column 1, line 52, delete "fludity" and insert --fluidity--.

Column 1, line 66, after "DD 209340," insert --DD 209338,--.

Column 1, line 68, delete "along" and insert --alone--.

UNITED STATES PATENT AND TRADEMARK OFFICE
CERTIFICATE OF CORRECTION

PATENT NO. : 5,129,950

DATED : July 14, 1992

INVENTOR(S) : Miklos Ghyczy et al.

It is certified that error appears in the above-identified patent and that said Letters Patent is hereby corrected as shown below:

Column 2, line 2, delete "houshold" and insert --household--.

Column 2, line 36, after "6" insert --carbon atoms and $R^2$ is an alkyl with 1 to 3 carbon atoms, a hydroxyalkyl with 1 to 3--.

Column 2, line 56, delete "disk" and insert --dish--.

Column 3, line 15, delete "means" and insert --mean--.

Column 3, lines 21-22, delete "radioactivity" and insert --radioactively--.

Column 3, line 68, delete "fementation" and insert --fermentation--.

Column 4, line 10, after "therewith" insert -- , --.

Column 4, line 55, delete "$R_2$" and insert --$R_1$--.

Column 5, line 16, delete "compunds" and insert --compounds--.

Column 5, line 18, delete "hexacholorbenzene" and insert --Hexachlorobenzene--.

UNITED STATES PATENT AND TRADEMARK OFFICE
CERTIFICATE OF CORRECTION

PATENT NO. : 5,129,950  
DATED : July 14, 1992  
INVENTOR(S) : Miklos Ghyczy et al.

Page 3 of 8

It is certified that error appears in the above-identified patent and that said Letters Patent is hereby corrected as shown below:

Column 5, line 19, delete "2,4-2,4,5,6" and insert --2,4,5,6--.

Column 5, line 22, delete "1,3,5,6" and insert --2,3,5,6--.

Column 5, line 46, delete "ethyltho" and insert --ethylthio--.

Column 5, line 61, delete "methyl" and insert --methylene--.

Column 5, line 63, delete "diemthyldithiocarbamate," and insert --dimethyldithiocarbamate,--.

Column 6, line 3, "Rabenazol," should be on the next line by itself.

Column 6, line 13, "Fenfuram," should be on the next line by itself.

Column 6, line 14, "methfuroxam" should be on the next line by itself.

Column 6, line 25, "Cetactaelat," should be on the next line by itself.

Column 6, line 27, "Chlormethionat," should be on the next line by itself.

UNITED STATES PATENT AND TRADEMARK OFFICE
CERTIFICATE OF CORRECTION

PATENT NO. : 5,129,950
DATED : July 14, 1992
INVENTOR(S) : Miklos Ghyczy et al.

It is certified that error appears in the above-identified patent and that said Letters Patent is hereby corrected as shown below:

Column 6, line 5, delete "fungiciide" and insert --fungicide--.

Column 6, line 10, delete "Chloroaniformethan" and insert --Chloraniformethan--.

Column 6, lines 11 and 12, delete "phenyltrichloro-phenyltrichloroacetataldehydanimal" and insert --phenyltrichloroacetataldehyd-aminal--

Column 6, line 41, delete "hydantion" and insert --hydantoin--.

Column 6, line 44, delete "(5-methyl" and insert --5.-methyl--.

Column 6, line 59, delete "deseases" and insert --diseases--.

Column 6, line 66, delete "carphphilum" and insert --carpophilum--.

Column 6, line 68, delete "Cladosproium" and insert --Cladosporium--.

Column 7, line 1, delete "carphophilum" and insert --carpophilum--.

UNITED STATES PATENT AND TRADEMARK OFFICE
CERTIFICATE OF CORRECTION

PATENT NO. : 5,129,950                                    Page 5 of 8
DATED     : July 14, 1992
INVENTOR(S) : Miklos Ghyczy et al.

It is certified that error appears in the above-identified patent and that said Letters Patent is hereby corrected as shown below:

Column 7, lines 2 and 3, delete "Collectotrichum" and insert --Colletotrichum--.

Column 7, line 8, delete "diseases" and insert --disease--.

Column 7, line 11, delete "Bymnosporangium" and insert --Gymnosporangium--.

Column 7, line 12, delete "Helminthosprorium" and insert --Helminthosporium--.

Column 7, line 30, delete "agenst" and insert --agents--.

Column 7, line 30, delete "surfact" and insert --surface--.

Column 7, line 68, after "herbicides" insert --such as--.

Column 9, line 64, delete "diichlorophenyl" and insert --dichlorophenyl--.

Column 10, line 13, delete "monochlloroacetic" and insert --monochloroacetic--.

Column 10, line 58, delete "dichlroobenzonitrile" and insert --dichlorobenzonitrile--.

UNITED STATES PATENT AND TRADEMARK OFFICE
CERTIFICATE OF CORRECTION

PATENT NO. : 5,129,950

DATED : July 14, 1992

INVENTOR(S) : Miklos Ghyczy et al.

It is certified that error appears in the above-identified patent and that said Letters Patent is hereby corrected as shown below:

Column 13, line 54, delete "example" and insert --examples--.

Column 15, line 40, delete "Convolutuss" and insert --Convolutus--.

Column 15, line 48, delete "trivalis," and insert --trivialis,--.

Column 15, line 51, delete "Gallium" and insert --Galium--.

Column 15, line 52, delete "Girsium" and insert --Cirsium--.

Column 16, line 2, delete "cyanimide" and insert --cyanamide--.

Column 16, line 10, delete "kierserit" and insert --kieserit--.

Column 16, line 62, delete "applicatoion" and insert --application--.

Column 16, line 63, delete "conditoons" and insert --conditions--.

Column 17, line 17, before "combination" insert --a--.

UNITED STATES PATENT AND TRADEMARK OFFICE
CERTIFICATE OF CORRECTION

PATENT NO.  : 5,129,950
DATED       : July 14, 1992
INVENTOR(S) : Miklos Ghyczy et al.

It is certified that error appears in the above-identified patent and that said Letters Patent is hereby corrected as shown below:

Column 17, line 38, delete "sprayying" and insert --spraying--.

Column 19, line 34, before "state" insert --wet--.

Column 22, line 17, after "effectiveness" insert --of both products was different--.

Column 22, line 58, "18" should begin a new paragraph.

Column 23, line 57, after "Desirably" insert -- , --.

Column 23, line 57, after "as" insert --dense--.

Column 23, line 64, delete "<1<2<3" and insert --<1<2≦3--.

Column 23, line 68, delete "<1<3<2" and insert --<1≦3<2--.

Column 24, line 4, delete "1, 3<2" and insert --1, 3≦2--.

Column 24, line 7, delete "lost" and insert --lots--.

Column 24, line 49, "120" should start a new paragraph.

UNITED STATES PATENT AND TRADEMARK OFFICE
CERTIFICATE OF CORRECTION

PATENT NO. : 5,129,950

DATED : July 14, 1992

INVENTOR(S) : Miklos Ghyczy et al

It is certified that error appears in the above-indentified patent and that said Letters Patent is hereby corrected as shown below:

Column 26, lines 44-45, delete "speed is improved by 42 and 48% over usual yeast growth--.

Signed and Sealed this

Nineteenth Day of April, 1994

Attest:

BRUCE LEHMAN

Attesting Officer

Commissioner of Patents and Trademarks